United States Patent
Schlögl et al.

(10) Patent No.: US 6,904,128 B2
(45) Date of Patent: Jun. 7, 2005

(54) DEVICE FOR COOLING SURFACE THAT ROTATES ABOUT A ROTATION AXIS AND THAT FACES THE ROTATION AXIS

(75) Inventors: Andreas Schlögl, Ottobrunn (DE); Peter Tichy, Uttenreuth (DE); Eckhard Wolfgang, Munich (DE)

(73) Assignee: Siemens Aktiengesellschaft, Munich (DE)

(*) Notice: Subject to any disclaimer, the term of this patent is extended or adjusted under 35 U.S.C. 154(b) by 0 days.

(21) Appl. No.: 10/381,883

(22) PCT Filed: Sep. 20, 2001

(86) PCT No.: PCT/DE01/03641

§ 371 (c)(1),
(2), (4) Date: Sep. 12, 2003

(87) PCT Pub. No.: WO02/26132

PCT Pub. Date: Apr. 4, 2002

(65) Prior Publication Data

US 2004/0028185 A1 Feb. 12, 2004

(30) Foreign Application Priority Data

Sep. 29, 2000 (DE) .......................................... 100 48 488

(51) Int. Cl.$^7$ ................................................ H01J 35/10
(52) U.S. Cl. ...................................... 378/141; 378/130
(58) Field of Search ................................ 378/127, 130, 378/141, 199, 200; 313/17, 22, 35, 36, 12, 24; 239/7, 14

(56) References Cited

U.S. PATENT DOCUMENTS

| | | | |
|---|---|---|---|
| 4,064,411 A | * 12/1977 | Iwasaki et al. | 378/141 |
| 4,997,129 A | * 3/1991 | Waldrum | 239/7 |
| 5,299,249 A | 3/1994 | Burke et al. | |
| 2001/0048976 A1 | * 12/2001 | Hess | 427/421 |

FOREIGN PATENT DOCUMENTS

DE 199 45 415 4/2001

OTHER PUBLICATIONS

Patent Abstracts of Japan, 57162248, Oct. 6, 1982, Hitachi Ltd. Mori Takehiko (abstract only).
Patent Abstracts of Japan, 63064252, Mar. 22, 1988, Ulvac corp. Hattori Shuzo (Abstract only).

* cited by examiner

Primary Examiner—Edward J. Glick
Assistant Examiner—Chih-Cheng Glen Kao
(74) Attorney, Agent, or Firm—Young & Thompson

(57) ABSTRACT

A device (4) comprises a container (40) for a liquid coolant (41) that is disposed between the axis (1) and the surface (30) facing the axis to co-rotate with the surface. The device is further provided with an atomizer nozzle (42) of the container, facing the surface, from which the coolant is discharged during rotation of the container due to the centrifugal force (F) acting upon the coolant of the container in the form of an atomized jet (43) that strikes the surface. The device cools a surface of an electronic device (3) that runs hot, the electronic device supplying the X-ray source of a computer tomograph with power and rotating about the axis of the gantry (2) of the tomograph.

7 Claims, 2 Drawing Sheets

DEVICE FOR COOLING SURFACE THAT ROTATES ABOUT A ROTATION AXIS AND THAT FACES THE ROTATION AXIS

CROSS REFERENCE TO RELATED APPLICATIONS

This application is the 35 USC 371 national stage of international application PCT/DE01/03641 filed on Sep. 20, 2001, which designated the USA.

FIELD OF THE INVENTION

The invention relates to a device for cooling a surface that rotates about a rotation axis and that faces the rotation axis.

BACKGROUND OF THE INVENTION

An example of a surface to be cooled that rotates about a rotation axis and that faces the rotation axis is a surface of an electronic device that becomes hot, said electronic device supplying electrical power to the X-ray source of a computer tomograph and rotating together with the X-ray source about a tube designed to accommodate a patient to be examined. Such a system is also known as a "gantry".

With a computer tomograph of this type, it is desirable to achieve the highest possible rotational frequency, since on the one hand this enables the number of tomography examinations performed per time unit to be increased and on the other images of fast-moving organs (e.g. the heart) are possible free of artifacts.

The limiting variable for the maximum achievable rotational frequency is the total mass that is to be brought into rotation, which includes, inter alia, not only the X-ray detector but also the mass of the X-ray source, the mass of the device for supplying electrical power to the X-ray source and the mass of a device co-rotating with the X-ray source and serving to cool a surface of the device for supplying the electrical power, said surface becoming hot. The smaller this total mass is, the greater is the maximum achievable rotational frequency. At the same time the rotation radius can be reduced by reducing the size of components, resulting in an overall reduction in the centrifugal force.

A reduction of each individual mass contributing to the total mass in itself causes a reduction in the total mass, as does a reduction in the mass of the device for cooling a surface of the device that becomes hot, said device supplying electrical power to the X-ray source.

SUMMARY OF THE INVENTION

The invention specified in claim 1 advantageously provides a device for cooling a surface that rotates about an axis and that faces the axis, said device co-rotating with the surface and exhibiting a low-mass design.

The device according to the invention mainly comprises a container for a liquid coolant that is disposed between the axis and the surface to be cooled facing said axis to co-rotate with the surface, and at least one atomizer nozzle of the container that is turned toward the surface and from which the coolant is discharged during rotation of the container due to the centrifugal acting upon the coolant in the container in the form of an atomized jet that strikes the surface.

The device according to the invention cleverly uses the rotation to apply an efficient atomization cooling technique. In particular, the highly efficient and known technique of "spray cooling" with all its advantages can be employed, the centrifugal force advantageously being used as a "compressor". The centrifugal force acts on the coolant in the rotating container and generates a sufficiently high pressure which is enough to spray the coolant through the atomizer nozzle onto the surface to be cooled.

The device according to the invention is advantageously suitable for general use wherever a surface that rotates about an axis and that faces the axis is to be cooled, and at the same time, on account of its low mass, advantageously permits a high maximum achievable rotational frequency and/or an increase in the rotational frequency compared to the prior art owing to the reduction in centrifugal force.

An advantageous embodiment of the device according to the invention is implemented or could be implemented such that the atomized jet strikes the surface to be cooled obliquely at an angle rather than vertically. This can preserve/achieve an optimal homogeneity of the coolant sprayed onto the surface to be cooled and consequently an improved cooling effect.

In an advantageous development of this embodiment, the angle at which the atomized jet obliquely strikes the surface to be cooled can be set as a function of the rotational frequency of this surface.

An atomized jet obliquely striking the surface to be cooled at an angle is produced, for example, if the atomized jet is discharged from the atomizer nozzle using a spray axis that is aligned vertically relative to the surface. The atomized jet is deflected on its way from the nozzle to the surface to be cooled due to the effect of the Coriolis force in the plane of rotation and strikes the surface obliquely at an angle. The size of this angle depends on the rotational frequency and is all the greater, the greater the rotational frequency.

Notwithstanding this, an atomized jet striking the surface to be cooled obliquely at an angle can be produced in that the atomized jet is discharged from the atomizer nozzle with a spray axis aimed at such an oblique angle to the surface to be cooled that the atomized jet strikes the surface obliquely at an angle. In this case the angle at which the atomized jet obliquely strikes the surface to be cooled can, for example, be set by the angle of the spray axis relative to this surface. The last-mentioned angle can be set as a function of the rotational frequency of the surface.

An advantageous development of the device according to the invention features a closed-loop coolant device in which the atomized coolant in which the atomized coolant is collected after striking the surface to be cooled and channeled back to the container.

In a preferred and advantageous embodiment of this development, the closed-loop coolant device features a cooling surface on which coolant that has vaporized on the surface to be cooled condenses.

In a particularly preferred and advantageous embodiment of the device according to the invention, the surface to be cooled is a surface of an electronic device that becomes hot, said device rotating about a tube designed to accommodate a patient to be examined and serving to supply electrical power to the X-ray source of a computer tomograph.

As a further application it is also conceivable to use such a cooling device for cooling the target, i.e. the anode of the X-ray source itself, in a similar manner. Accordingly, an advantageous embodiment of the device according to the invention is implemented such that the surface to be cooled is a surface of a target that becomes hot, said target being that of an X-ray source of a computer tomograph rotating about a tube designed to accommodate a patient to be examined.

Advantages of each of these last-mentioned devices are:

the device can dissipate heat highly efficiently from the surface to be cooled of the device serving to supply electrical power to the X-ray source and/or the X-ray source itself;

its low mass reduces the total mass of the tomograph to be set into rotation (rotating part of the gantry) and permits a desired higher maximum achievable rotational frequency, which increases the efficiency of the tomograph by increasing the tomography examinations that can be performed per time unit and/or enables images of fast-moving organs to be generated free of artifacts;

it requires only that the device for supplying electrical power to the X-ray source is disposed such that its surface to be cooled is turned toward the rotation axis;

it permits the device for supplying electrical power to the X-ray source to be built using power electronics components, thereby once again reducing the total mass of the tomograph that is to be set into rotation and once again increasing the maximum achievable rotational frequency, with the result that the size of the rotating part of the tomograph and the rotation radius are considerably reduced.

BRIEF DESCRIPTION OF THE DRAWING

The invention is explained in greater detail in the following description with the aid of the drawings provided by way of example.

The figures are not to scale.

DETAILED DESCRIPTION OF THE INVENTION

Figure 1:
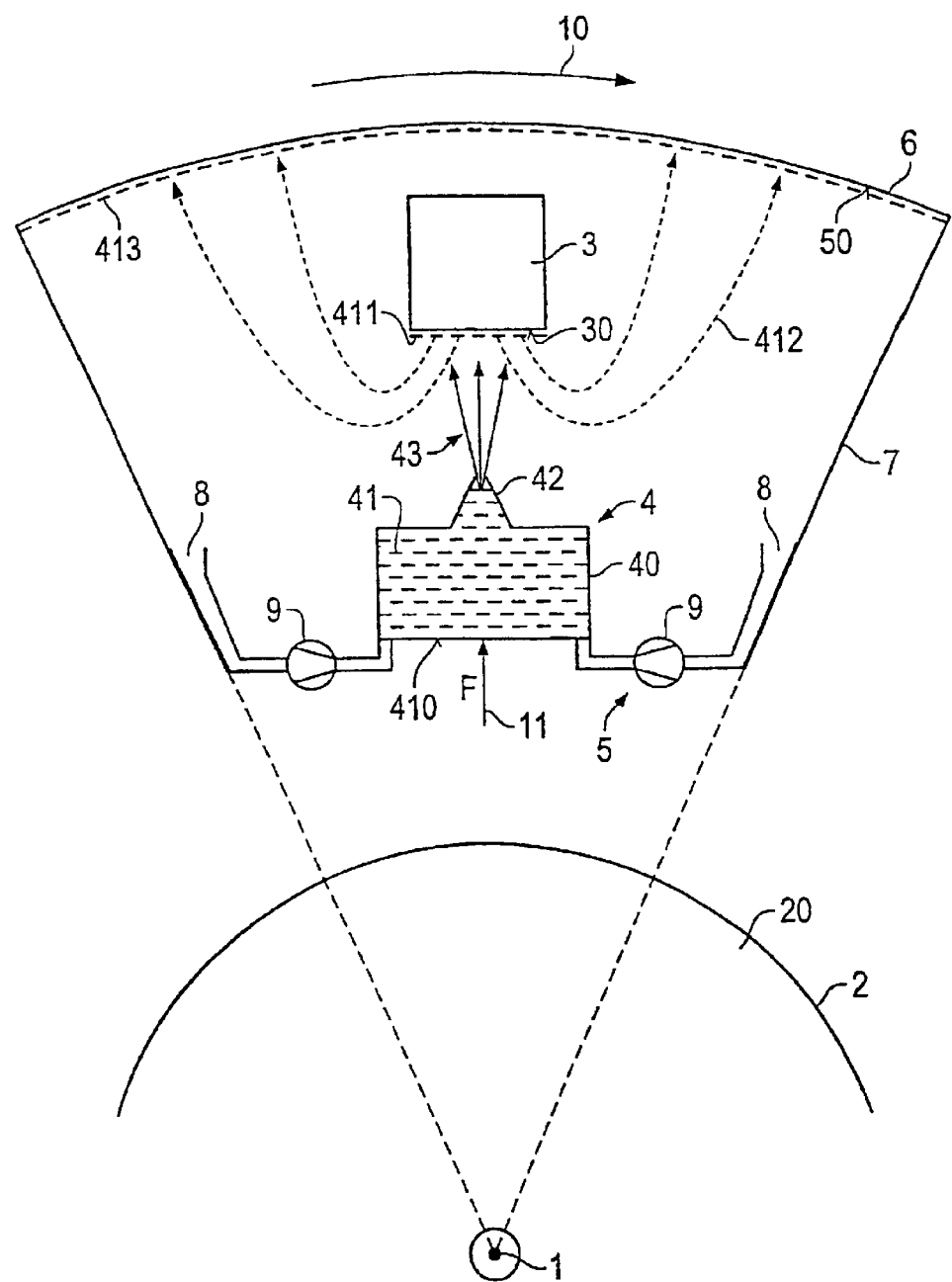
FIG. 1 shows a schematic representation of an embodiment of a device according to the invention for cooling a surface of the gantry that becomes hot and that is mounted on the rotating part of the gantry and co-rotates with this part.

The part of the gantry of an exemplary computer tomograph shown in FIG. 1 has an axis 1 which is positioned vertically relative to the drawing plane of FIG. 1 and about which the rotating part of the gantry of the tomograph revolves.

Axis 1 is at the same time a longitudinal axis of the merely indicated stationary tube 2 of the gantry, said tube serving to accommodate a patient. The accommodated patient is moved in the interior 20 of the tube 2 along the axis 1 which is also contained in the interior 20.

The part of the gantry of the tomograph rotating about the axis 1 and the tube 2 comprises, inter alia, an X-ray source, the X-ray detector, an electronic device for supplying electrical power to the X-ray source and a device for cooling a surface to be cooled of a device of the rotating part of the gantry, said device becoming hot. The device that becomes hot is represented symbolically in FIG. 1 by a box identified by 3. It is mounted on the rotating part of the gantry and co-rotates in synchronism with this part about the axis 1 and the tube 2, for example in the direction of the arrow 10.

The device 3 that becomes hot is, for example, the device for supplying electrical power to the X-ray source, preferably built using semiconductor components, the surface to be cooled being a surface of this device that becomes hot and that faces the axis 1, and/or the X-ray source itself, the surface to be cooled being a surface of the anode of this source that becomes hot and being turned toward the axis 1, said surface preferably being a backside surface of the grounded anode.

The surface to be cooled of the device 3 is symbolically represented in FIG. 1 by the side surface of the box identified by 30 that is turned toward the axis 1. The surface to be cooled 30 is, for example, positioned vertically relative to the drawing plane of FIG. 1.

The device for cooling the surface to be cooled 30 is identified by 4 and is disposed between the tube 2 and the surface to be cooled 30 of the device 3.

According to the invention, the device 4 for cooling the surface 30 of the device 3 comprises a container 40 for a liquid coolant 41 that is disposed between the tube 2 and the surface 30 of the device 3 to co-rotate with the device 3 and the surface 30, and at least one atomizer nozzle 42 of the container 40 that is turned toward the surface 30 and from which the coolant 41 is discharged during rotation of the container 40 in the form of an atomized jet 43 due to the centrifugal force F acting upon the coolant 41 in the container 40, said atomized jet 43 striking the surface 30 of the device 3.

Since the container 40 is disposed between the tube 2 and the surface 30 of the device 3 and the axis 1 is located in the interior 20 of the tube 2, the container 40 is necessarily disposed between the axis 1 and the surface to be cooled 30 that is turned toward this axis, which, ultimately, is what matters.

The co-rotation of the container 40 with the device 3 and the surface 30 means that the container 40 rotates about the axis 1 in synchronism with the device 3 and the surface 30 in the direction of the arrow 10, for example owing to the fact that the container 40 and the device 3 are permanently joined to each other.

The centrifugal force F generated during the rotation of the container 40 about the axis 1 and acting upon the coolant 41 in the container 40 acts radially in the direction away from the axis 1, i.e. in the direction of the arrow 11. The amount of the centrifugal force F is given by the equation $|F|=m \cdot r \cdot \omega^2$, where m stands for the mass of the coolant 41, r for the radial distance of the coolant 41 from the axis 1 during the rotation, and $\omega$ for the angle speed of the rotation.

The centrifugal force F acting vertically upon the surface 410 that is turned toward axis 1 of the liquid coolant 41 in the container 40 generates a hydrostatic pressure in the coolant 41 that causes the coolant 41 to be discharged from the atomizer nozzle 42 in the form of the atomized jet 43, by means of which the coolant 41 is sprayed onto the surface to be cooled 30 of the device 3 in the form of small coolant particles.

Owing to the rotation it is known that the Coriolis force acts upon each coolant particle of the atomized jet 43 moving from the atomizer nozzle 42 toward the surface 30, said force being directed in the opposite direction to the arrow 10 and deflecting the coolant particle in this opposite direction. This causes the atomized jet 43, or more accurately a spray axis of the atomized jet 43, to be deflected en route between the atomizer nozzle 42 and the surface to be cooled 30.

Figure 2:
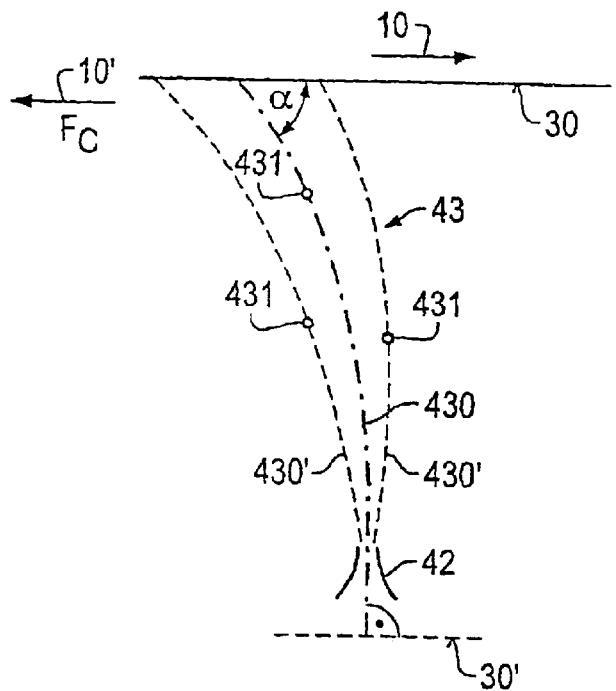
FIG. 2 shows a schematic representation showing the atomized jet discharged from an atomizer nozzle of the embodiment of the device according to the invention with a spray axis that is vertical relative to the surface to be cooled, said jet striking the surface obliquely at an angle due to the Coriolis force acting upon it.

This is shown in slightly exaggerated form in FIG. 2. It is assumed, for example, that the atomized jet 43 is discharged from the atomizer nozzle 42 with a spray axis 430 aligned vertically relative to the surface to be cooled 30. This is indicated in FIG. 2 by the fact that in the area of the atomizer nozzle the spray axis 430, represented by a dash-dotted line, is vertical with respect to a conceptual surface 30' represented by a dashed line and running parallel to the surface to be cooled 30 and positioned vertically relative to the drawing plane of FIG. 2.

A coolant particle 431 being discharged from the atomizer nozzle 42 and moving along the spray axis 430 does not continue in a straight line en route to the surface 30, but is deflected due to the Coriolis force $F_c$ acting in the direction of the arrow 10' contradirectionally to the arrow 10 and moves on a path deflected to the left in FIG. 2, which defines the now deflected spray axis or spray trajectory 430 of the atomized jet 43.

Similarly, coolant particles 431 of the atomized jet 43 (?) not located on the spray axis 430 move laterally with respect to the spray axis 430 on deflected paths relative to the surface 30, as indicated by dashed lines 430'. Thus, the atomized jet 43 is deflected overall and strikes this surface 30 obliquely at an angle. This angle is represented in FIG. 2 by the angle $\alpha<90°$ between the spray axis 430 striking the surface 30 and this surface 30.

If the atomized jet 43 strikes the surface 30 at an oblique angle, this favors the attainment of an optimal homogeneity of the coolant 41 sprayed onto the surface 30, since the impetus transmitted each time to the surface 30 from the moving coolant particles 431 is not directed precisely radially, but also has a component parallel to the surface 30 which encourages the sprayed-on coolant to flow in the direction of this component.

The angle $\alpha$ depends on the angle speed $\omega$ of the rotation and therefore on the rotational frequency. If this is unsuitable for achieving a sufficiently small angle $\alpha<90°$, a way to assist is by causing the atomized jet 43 to discharge from the atomizer nozzle 42 with a spray axis 430 aligned obliquely at an angle relative to the surface to be cooled 30.

Figure 3:
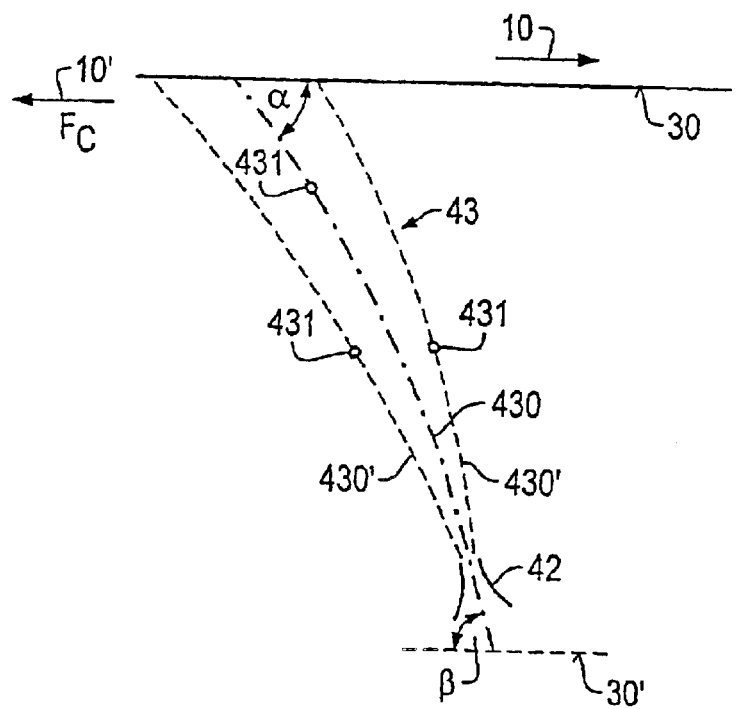
FIG. 3 shows a schematic representation showing the atomized jet discharged from an atomizer nozzle of the embodiment of the device according to the invention with a spray axis aligned obliquely at an angle to the surface to be cooled, said jet striking the surface obliquely at an angle.

A case of this type is shown in FIG. 3. FIG. 3 differs from FIG. 2 only in that the spray axis 430 is tilted in the area of the atomizer nozzle 42 contradirectionally to the direction of rotation 10 obliquely at an angle $\beta<90°$ to the left with respect to the level 30. The smaller the angle $\beta$ is chosen, the smaller is the angle $\alpha$.

In this case the angle $\alpha$ can be set as a function of the rotational frequency by setting the angle $\beta$, particularly to a value that is always optimal for cooling the surface 30.

Instead of only one atomizer nozzle 42, two or a plurality of atomizer nozzles 42 can be present, their atomized jets 43 particularly striking the surface 30 obliquely from different directions.

The surface to be cooled 30 can, for example, also be disposed obliquely relative to a radially aligned atomizer nozzle 42 and furthermore does not have to be level, but can be bent into a convex and/or concave shape.

The device 4 shown in FIG. 1 for cooling the surface 30 of the device 3 exhibits a closed-loop coolant device 5 in which the atomized coolant 41 is collected after striking the surface to be cooled 30 and returned to the container 40. In particular, this closed-loop device 5 exhibits a cooling surface 50 on which coolant 41 which has vaporized on the surface to be cooled 30 condenses.

The device operates, for example, as follows: The coolant 41 constantly sprayed onto the surface to be cooled 30 forms a coolant film 411 on this surface 30, from which coolant 41 constantly vaporizes; said coolant film 411 being indicated by a dashed line.

Due to the centrifugal force F, the resulting coolant vapor 412 indicated by dashed arrows moves radially away from the axis 1, as indicated by the deflection of the dashed arrows, and reaches a co-rotating wall 6 which closes off the rotating parts of the tomograph radially toward the outside and is preferably bent around the axis 1, said wall for example being cooled by a self-generating airstream produced during the rotation.

The surface of the wall that is turned toward the axis 1 forms the cooling surface 50, which is reached by the coolant vapor 412 and on which the coolant vapor 412 is deposited as a coolant condensate which forms a coolant film 413 that is spread evenly over the entire cooling surface 50, said film being pressed against the cooling surface 50 by the centrifugal force F.

If the rotational frequency were to be stepped down, the coolant 41 contained in the coolant film 413 could automatically flow away, for example via side walls 7, in the direction of axis 1, collected in collecting funnels 8 and returned by the collecting funnels 8 to the container 40.

The collected coolant 41 can be returned if necessary, e.g. during constant rotation of the gantry, with the aid of pumps 9. However, such pumps 9 complicate the design of the device 4 and increase the mass to be set into rotation.

An inert coolant that does not react chemically with the parts with which it comes into contact is preferably used as coolant 41. Fluorinert can be used, for example.

In the prior art, the device 3 for supplying electrical power to the X-ray source of the tomograph is constructed using standard components and power electronics modules that are relatively heavy and have a low ratio of chip to package mass.

Cooling is effected by means of active air or water cooling, the water cooling solution operating more effectively but also implying a higher technical overhead and being associated with larger masses. However, air cooling also means considerable volume, and therefore weight, as a result of the necessary heat storage capacity of the heatsink.

In the case of the novel tomograph equipped with the device 4 according to the invention for cooling the surface 30 of the device 3, there is the additional possibility that the device 3 advantageously features not the relatively heavy cooling components and modules exhibiting a low ratio of chip to package mass, but power electronics components of lightweight design, thereby once again reducing the tomograph mass that is to be set into rotation and further simplifying the design of the rotating part of the tomograph.

The device according to the invention for cooling a surface that rotates about a rotation axis and that faces the rotation axis is not limited to the application in a tomograph.

What is claimed is:

1. Device (4) for cooling a surface (30) that rotates about an axis (1) and that faces the axis (1), which comprises
    a container (40) for a liquid coolant (41) that is disposed between the rotation axis (1) and the surface (30) for a co-rotation with the surface (30), and
    at least one atomizer nozzle (42) of the container (40) which faces the surface (30) and from which the coolant (41) is discharged during rotation of the container (40) due to the centrifugal force (F) acting upon the coolant (41) in the container (40) in the form of an atomized jet (43) that strikes the surface (30).

2. Device according to claim 1, the atomized jet (43) striking the surface to be cooled (30) obliquely at an angle ($\alpha$).

3. Device according to claim 2, the angle ($\alpha$) at which the atomized jet (43) obliquely strikes the surface to be cooled (30) being selectable as a function of the rotational frequency of this surface (30).

4. Device according to claim 1, comprising a closed-loop coolant device (5) in which vaporized coolant (41) is collected after striking the surface to be cooled (30) and returned to the container (40).

5. Device according to claim 4, the closed-loop coolant device (5) featuring a cooling surface (50) on which coolant (412) which has vaporized on the surface to be cooled (30) condenses.

6. Device according to claim 1, the surface to be cooled (30) being a surface that becomes hot of an electronic device for supplying electrical power to an X-ray source of a computer tomograph, said electronic device rotating about a tube (2) for accommodating a patient to be examined.

7. Device according to claim 1, the surface to be cooled (30) being a surface that becomes hot of a target of an X-ray source of a computer tomograph rotating about a tube designed to accommodate a patient to be examined.

* * * * *